(12) United States Patent
Sells, II

(10) Patent No.: US 6,488,031 B1
(45) Date of Patent: *Dec. 3, 2002

(54) VISUAL CUE FOOT FLOATER FOOT POSITIONER

(76) Inventor: Haskell Lee Sells, II, 3900 Yew Cir., Raleigh, NC (US) 27612

( * ) Notice: Subject to any disclaimer, the term of this patent is extended or adjusted under 35 U.S.C. 154(b) by 0 days.

This patent is subject to a terminal disclaimer.

(21) Appl. No.: 08/411,084

(22) Filed: Mar. 27, 1995

(51) Int. Cl.[7] .................................................. A61F 5/37
(52) U.S. Cl. .......................... 128/846; 128/882; 5/648; 5/649
(58) Field of Search ................................. 128/846, 869, 128/882; 602/23, 28; 5/648, 649

(56) References Cited

U.S. PATENT DOCUMENTS

| | | | | |
|---|---|---|---|---|
| 4,090,268 A | * | 5/1978 | Turner | 5/648 |
| 4,135,504 A | * | 1/1979 | Spann | 5/648 |
| 4,278,079 A | * | 7/1981 | Simhoni | 5/649 |
| 5,125,123 A | * | 6/1992 | Engle | 128/882 |

* cited by examiner

Primary Examiner—Michael A. Brown

(57) ABSTRACT

In the healthcare field there are specific wounds generally referred to as "pressure ulcers" or "decubitus ulcers". These wounds are generally caused by: direct constant pressure to body tissues; internal disease or disorders which surfaces on the skin; urine or fecal material constantly in contact with skin causing breakdown; lack of proper nutrition; or, a combination of all these factors. These wounds occur mostly on "bed-ridden patients" whose debilitation is such that they cannot react to their body's neurological signals for them to adjust their position. Most of these patients are prone and lay on standard mattresses.

These "pressure ulcers" can occur in any area of the body but are predominantly found in the shoulders, coccyx, hip, legs, and heels. Actually, any "bony-prominence" is a candidate for breakdown if pressure is allowed to be against it constantly.

There have been many attempts to "cure" or "treat" these "pressure ulcers". There are nursing attempts to turn the patient every two hours to prevent these wounds from occuring. There have been products produced to give "floatation" to these patients to help relieve pressure. These products range from low air loss active floatation beds to static air mattresses to foam (trapped air) overlays to body positioners.

1 Claim, 2 Drawing Sheets

VISUAL CUE FOOT FLOATER FOOT POSITIONER

FIELD OF THE INVENTION

This invention relates to the problem of "pressure ulcers" of the heel area. This invention relates to foot positioners and more particularly to a practical, effective method of positioning feet to help prevent skin and heel breakdown which leads to the formation of pressure ulcers on the heel.

BACKGROUND

In the past, foot positioners have consisted of such items as standard pillows, air filled boots, "bean-bag" cushions, and foam cradles. The problems with these "manufactured products" include; difficulty in determining for which foot the positioner is indicated; quick visual assessment of skin on the foot (due to the foot being "wrapped in" the positioner); heat build up causing odor and discomfort; maintaining proper heel positioning; consequence of straps being too tight (causing breakdown) or too loose (non-functional); and,choosing the correct size. Pillows have their own set of problems in that they are not clearly defined as a "foot" product; they do not stay in position; they can be too high, possibly causing a hyper-extended knee; they can be too low, accomplishing nothing.

An appropriate positioner should be cool, comfortable, and well accepted by the patient. It should provide the healthcare personnel immediate visual assessment of the patient's foot position and skin condition. It should be uniform in it' size so that there is no guessing on the part of the healthcare personnel as to sizing, it should be a "one size fits all". It should be non-incapsulating to help prevent heat build up or pressure from straps. It should be a low profile positioner to help prevent hyper-extention of the knee.

OBJECT

It is, therefore, an object of the present invention to provide a new and novel foot positioner for helping to protect patient's heels from breakdown.

Another object of the present invention is to make this positioner easily identifiable by healthcare staff as to its purpose; to provide immediate visual assement of the foot position and skin condition; to be uniform in its' size so that "one size fits all"; to be a low profile so as to help prevent hyper-extention of the knee; to allow the foot to be free, unencumbered by straps or encapsulating material;

SUMMARY OF THE INVENTION

A foot positioner, designed to assist in appropriate positioning of a patient whose heels have been identified as having the potential for skin breakdown, is placed under the ankle/heel area of the feet with the feet slightly beyond the body of the positioner. The product positions the patient in such a manner as to help prevent heels from maintaining pressure with the mattress. The positioner is passive in that it is strategically placed by a nurse (or other healthcare professional) so as to best benefit the patient. It will provide immediate visual assessment of the feet; it will be cool (that is, there will be no heat build up due to an incapsulating effect); it will be free of straps; it will be easily recognizable by the healthcare staff as intended for heel positioning.

DETAILED DESCRIPTION OF PRODUCT AND DRAWINGS

The invention is the design of the positions 10, in that the positioner is the first "hospital bed wide" positioner; the first designed to support both heels; the first low profile positioner for heels. While the design could be made from a variety of materials, the present design is composed of foam which is of a 1.45 density and an indentation load reflection of 36. (See FIGS. 1 and 3) The foam is cut 34 inches wide; 10 inches deep (with 6½ inches at 1¼ inch height and 3½ inches at a height of 3½ inches); The 3½ inch width section is cut into cubes 72 of 1⅞ inches square. The 6½ inch width portion 14 is flat. See FIG. 2 for actual positioning representation.

DETAILED DESCRIPTION OF PRODUCT AND DRAWINGS

Figure 1:
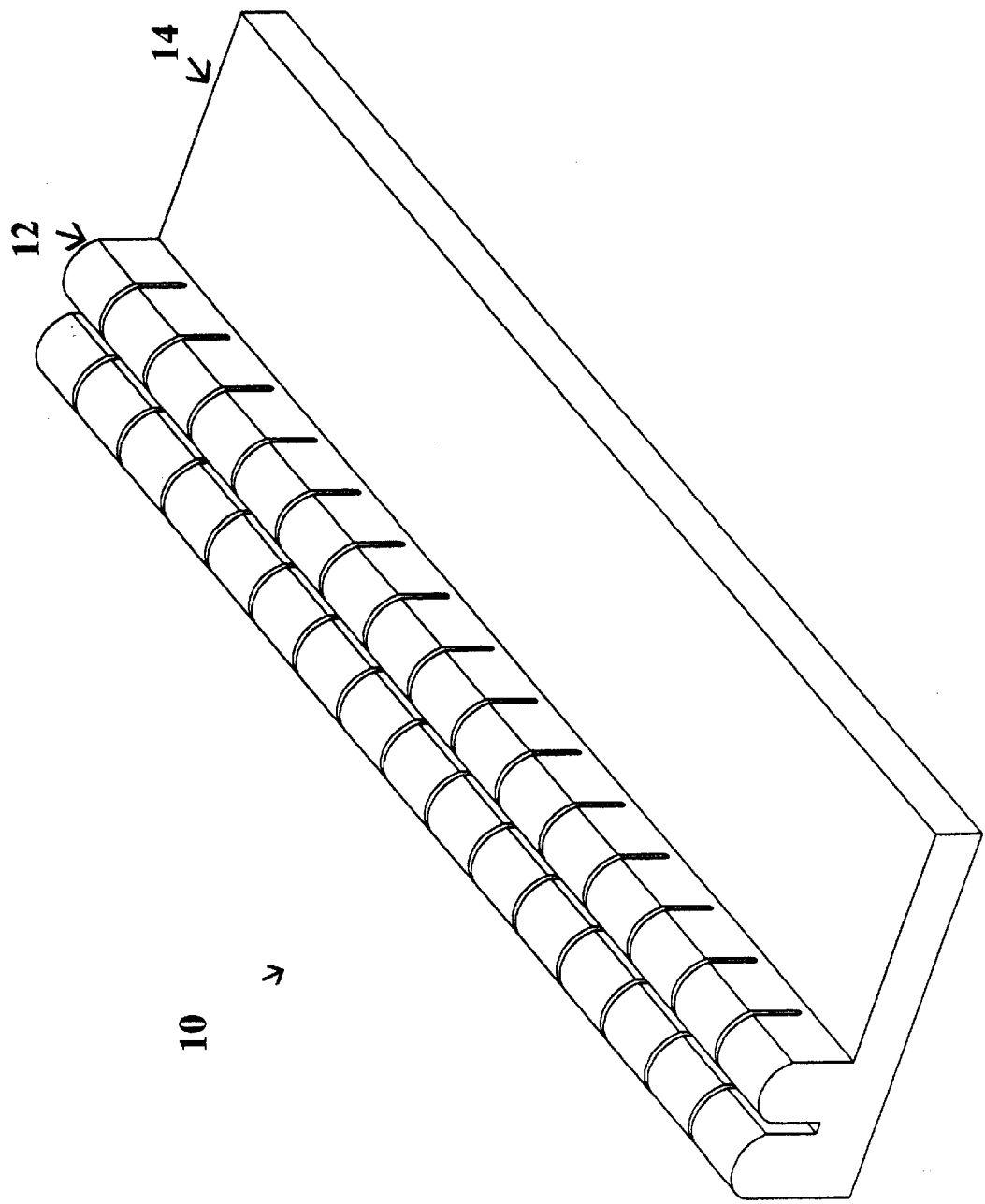
FIG. 1 is an isometric view of the positioner.
Figure 2:
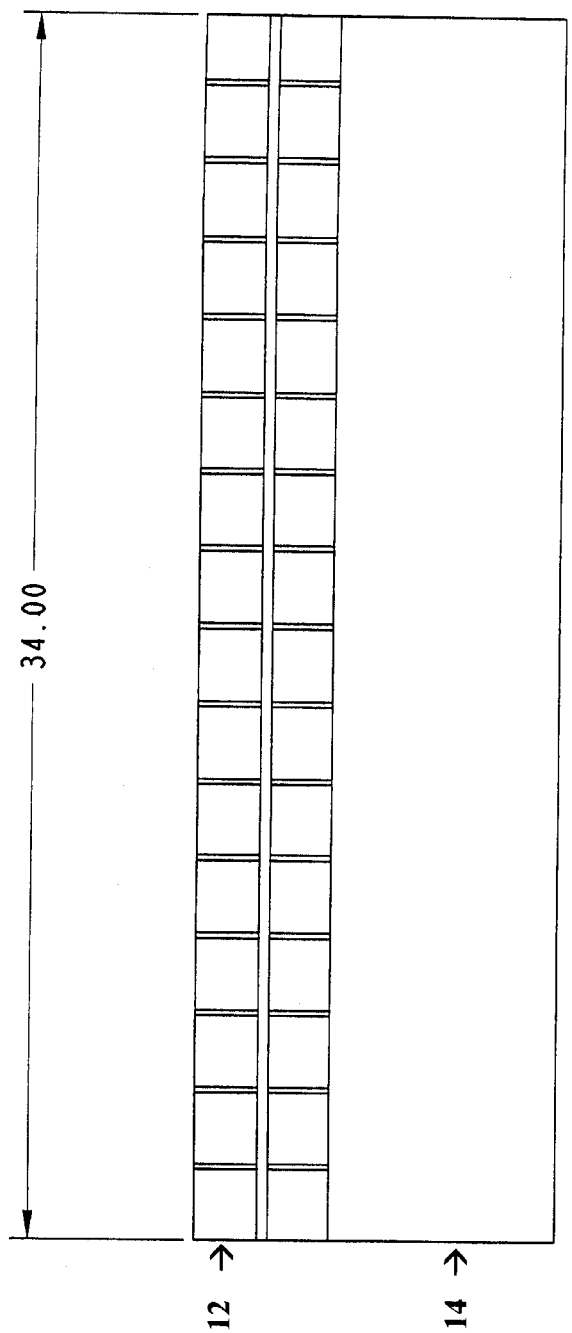
FIG. 2 is a top plan view of the positioner.
Figure 4:
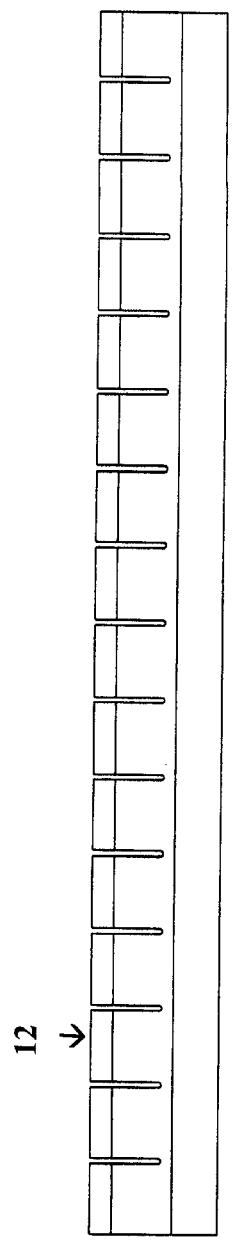
FIG. 4 is a rear elevation.
Figure 3:
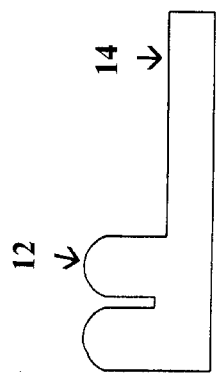
FIG. 3 is a side elevation of FIG. 1.

What is claimed is:

1. A therapeutic positioning device for preventing or assisting in the healing of ulcers and other skin breakdown of the heel and foot comprising a resilient body, said resilient body being constructed of a single rectangular layer of foam, said rectangular layer is thirty four inches in width and ten inches in length, said layer of foam is formed of individual cubic cells, said cells being one and seven eighth inch by one and seven eighth inch in dimensions and having one eighth inch gaps between each cell, said cells extending three and one half inches of the total length of said device and a flat layer of foam being one and one forth inch in thickness and extending six and one half inches of the device.

* * * * *